United States Patent [19]

Barton

[11] Patent Number: 4,699,978

[45] Date of Patent: Oct. 13, 1987

[54] SITE-SPECIFIC CHIRAL RUTHENIUM (II) AND COBALT (III) ANTITUMOR AGENTS

[75] Inventor: Jacqueline K. Barton, New York, N.Y.

[73] Assignee: The Trustees of Columbia University in the City of New York, New York, N.Y.

[21] Appl. No.: 693,019

[22] Filed: Jan. 18, 1985

[51] Int. Cl.$^4$ .................. C12Q 1/68; C07H 21/00; A61K 33/24; C07D 471/04

[52] U.S. Cl. .................. 536/27; 935/78; 204/157.72; 546/88; 435/6; 424/131

[58] Field of Search .................. 424/1.1, 9, 131, 149; 546/4, 10, 88; 556/136, 138; 536/22, 27; 435/6; 935/77, 78; 204/157.71, 157.72

[56] References Cited

U.S. PATENT DOCUMENTS 4,547,569 10/1985 Letsinger et al. ............... 536/27 X

OTHER PUBLICATIONS

Pope, L. M., et al, *J. Biol. Chem.*, vol. 257, Oct. 1982, pp. 12121–12128.
Barton, J. K., et al, *J. Am. Chem. Soc.*, vol. 106, No. 7, 1984, pp. 2172–2176.
Chang, C. H., et al, *Biochemistry*, vol. 21, 1982, pp. 6332–6334.
Barton, J. K., et al, *J. Am. Chem. Soc.*, vol. 104, No. 18, 1982, pp. 4967–4969.
Chang, C. H., et al, *Biochemistry*, vol. 23, 1984, pp. 2268–2274.
Pommier, Y. et al, *Biochemistry*, vol. 23, No. 14, 1984, pp. 3194–3201.
Letsinger, R. L. et al, *J. Am. Chem. Soc.*, vol. 103, 1981, pp. 7394–7396.

*Primary Examiner*—Esther M. Kepplinger
*Assistant Examiner*—Jeremy M. Jay
*Attorney, Agent, or Firm*—John P. White

[57] ABSTRACT

This invention concerns a coordination complex of the formula $(R)_2$—M—$(Y)_2$ wherein M comprises a suitable transition metal, e.g. cobalt or ruthenium, R comprises 1,10-phenanthroline or a substituted derivative thereof, Y comprises a labile ligand, e.g. chloride, tartrate, malonate or ascorbate ion and R and Y are bonded to M by coordination bonds.

A complex of this invention may be used for covalently labeling DNA with a complex of the formula $(R)_2$—M, wherein R and M are as previously defined. A complex of this invention which contains cobalt may also be used in a method for nicking DNA by effecting single-stranded scission of at least one phosphodiester bond of the DNA with ultraviolet radiation.

A complex of this invention is further useful in a method for killing tumor cells. A pharmaceutical composition for the treatment of tumor cells in a subject may be prepared containing an effective anti-tumor amount of a complex of this invention and a pharmaceutically acceptable carrier. Such a composition may be used for treating a subject afflicted with tumor cells so as to cause regression of the tumor cells.

10 Claims, 2 Drawing Figures

SITE-SPECIFIC CHIRAL RUTHENIUM (II) AND COBALT (III) ANTITUMOR AGENTS

The invention described herein was made with government support under grant number GM 33309 from the National Institutes of Health, United States Department of Health and Human Services. The government has certain rights in this invention.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Recently there has been increased attention focused on the binding of metal complexes to nucleic acids and nucleic acid constituents (1). This interest stems in large part from the successful application of cis-dichlorodiammineplatinum(II) (cis-DDP or cisplatin) as an antitumor drug (2). See also, U.S. Pat. Nos. 4,273,755 (1981); 4,302,446 (1981); 4,310,515 (1982); 4,339,437 (1982) and 4,451,447 (1984). More recently chiral transition metal complexes have been utilized in designing specific probes for nucleic acid structure. The tris(phenanthroline) complexes of zinc(II) (3) and ruthenium(II) (4) display enantiomeric selectivity in binding to DNA by intercalation. Because of their high specificity in intercalative binding to right- or left-handed DNAs, enantiomers of tris(4,7-diphenylphenanthroline) ruthenium(II) and cobalt(III) provide respectively spectroscopic probes (5) and cleaving agents (6) that are DNA conformation-specific. Such complexes bind to DNA only under suitable intercalating conditions, and do not bind to DNA in a covalent fashion.

It has now been discovered that certain bis-substituted metal complexes of phenanthrolines are capable of binding covalently and stereospecifically to DNAs. Such complexes are useful in stereospecific labeling and cleavage of DNAs and are further useful as antitumor agents.

SUMMARY OF THE INVENTION

This invention involves a coordination complex of the formula $(R)_2—M—(Y)_2$ wherein R comprises 1,10-phenanthroline or a substituted derivative thereof; M comprises a suitable transition metal, e.g. ruthenium or cobalt; Y comprises a labile ligand, e.g. chloride, tartrate, malonate or ascorbate ion; and R and Y are bonded to M by coordination bonds.

This invention also concerns a method for covalently labeling DNA with a complex of the formula $(R)_2—M$, where R and M are as defined above. This method involves contacting the DNA with a complex of this invention under suitable binding conditions such that complex covalently binds to the DNA.

This invention further concerns a labeled DNA molecule comprising DNA to which a complex of the formula $(R)_2—M$ is covalently bound wherein R comprises 1,10-phenanthroline or a substituted derivative thereof, M comprises a transition metal, e.g. ruthenium or cobalt, and R is bonded to M by a coordination bond.

This invention further concerns a method for nicking DNA by effecting single-stranded scission, i.e. breakage of at least one of the phosphodiester bonds along the DNA. This method involves contacting the DNA with a cobalt-containing complex of this invention under suitable binding conditions such that the complex covalently binds to the DNA to form an adduct and irradiating the adduct so formed with a sufficient dose of ultraviolet radiation of an appropriate wavelength to nick the DNA. An appropriate wavelength for the ultraviolet radiation of this method is a wavelength of ultraviolet radiation absorbed by the ligand bands of the complex used.

Another embodiment of this invention is a method for killing a portion of a population of appropriate tumor cells. This method involves contacting the tumor cells under suitable conditions with an effective amount of a coordination complex of this invention to kill the tumor cells. Where the tumor cells are present in a subject, e.g. a human or animal, the contacting may suitably be effected by administering the coordination complex to the subject. Where the complex used in this embodiment is a cobalt-containing complex the method may further involve irradiating the tumor cells with a suitable dose of ultraviolet radiation of an appropriate wavelength at a suitable time after the tumor cells have been contacted with the complex, permitting the complex to nick DNA.

This invention further involves a pharmaceutical composition for the treatment of tumor cells in a subject which comprises an effective antitumor dose of a complex of this invention and a pharmaceutically acceptable carrier.

This invention additionally concerns a method for treating a subject, e.g. a human or animal, afflicted with tumor cells so as to cause regression of the tumor cells. This method involves administering to the subject by a suitable route a pharmaceutical composition of this invention in an amount sufficient to cause regression of the tumor cells. Administration may be parenteral or may be topical. Furthermore as in previous embodiments, where the complex is a cobalt-containing complex the method may further involve irradiating the tumor cells with a suitable dose of ultraviolet radiation of an appropriate wavelength. In this method the tumor cells may be irradiated at a suitable time after administration of the pharmaceutical composition to the subject permitting the complex to nick DNA.

DETAILED DESCRIPTION OF THE INVENTION

Figure 1:
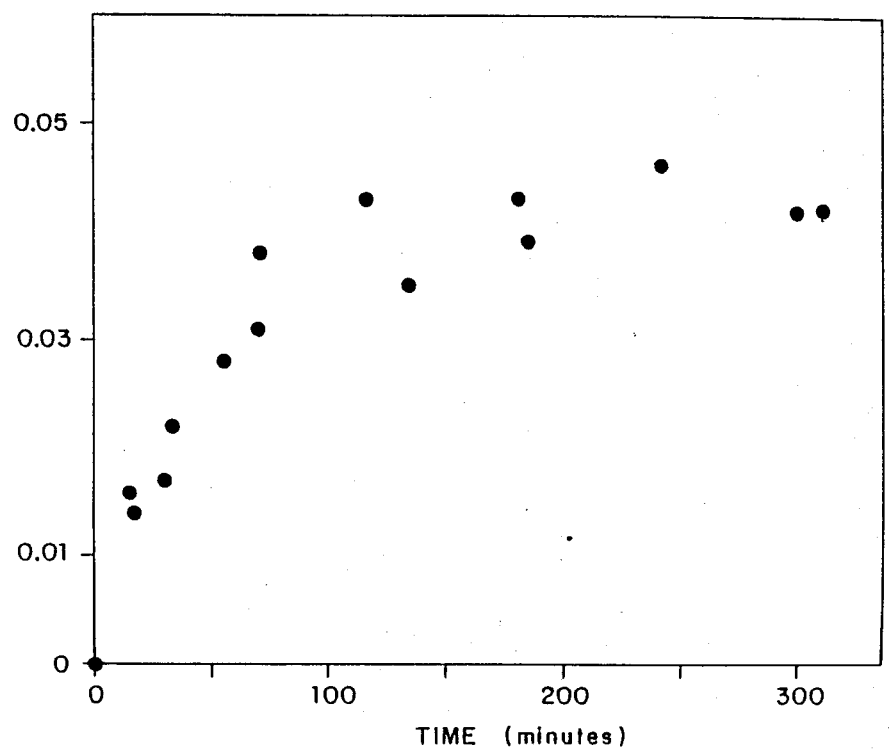
FIG. 1: Plot of (1,10-phenanthroline)$_2$RuCl$_2$ binding to calf thymus DNA as a function of time; r is the ratio of bound ruthenium to nucleotide concentrations.

The present invention involves a coordination complex of the formula $(R)_2—Co(III)—(Y)_2$ wherein R comprises 1,10-phenanthroline or a substituted derivative thereof; Y comprises a labile ligand, e.g. chloride, tartrate, malonate or ascorbate ion, and R and Y are bonded to the Co(III) by coordination bonds. A "substituted derivative" as the phrase is used herein is a compound obtained by replacing one or more hydrogen atoms present in 1,10-phenanthroline with one or more moieties having the characteristic that the complex containing the resulting compound binds to DNA. Merely by way of example, the substituted derivative of 1,10-phenanthroline may be 4,7-diamino-1,10-phenanthroline; 3,8-diamine-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline or 3,8-dispermine-1,10-phenanthroline. Unless otherwise specified, the complex of this invention is a racemic mixture of enantiomers.

Several such complexes including bis(1,10-phenanthroline)ruthenium(II) dichloride, bis(4,7-diphenyl-1,10-phenanthroline)-ruthenium(II) dichloride, and bis(4,7-diphenyl-1,10-phenanthroline)cobalt(III) tartrate have been prepared and their DNA-binding properties studied. Each of these neutral species is chiral, octahedral, and contains two inert ligands (the diamines) and two labile ligands in a cis-orientation.

One embodiment involves a method for covalently labeling DNA with a complex of the formula $(R)_2—M$ where R is as defined above, M in this and other embodiments of the invention is a suitable transition metal, i.e. a transition metal capable of forming an octahedral complex with 1,10-phenanthroline or a substituted derivative thereof and R is bound to M by a coordination bond. Presently preferred transition metals are ruthenium(II) and cobalt(III). According to this method the DNA is contacted with a complex of the formula $(R)_2—M—(Y)_2$, where R, M and Y are as defined above, the contacting being under suitable conditions such that the $(R)_2—M$ complex covalently bonds to the DNA.

The invention also concerns a labeled DNA molecule comprising DNA to which a complex of the formula $(R)_2—M$ as defined previously, is covalently bound. Preferably, the labeled DNA is produced by the method described above.

A further embodiment of this invention concerns a method for nicking DNA by effecting single-stranded scission, i.e. breakage, of at least one phosphodiester bond along the DNA. This method involves contacting the DNA with a cobalt(III)-containing complex of the formula $(R)_2—Co(III)—(Y)_2$, as previously defined, the contacted being under suitable conditions such that the $(R)_2—Co(III)$ complex covalently bonds to the DNA to form an adduct. The adduct so formed is then irradiated with a sufficient dose of ultraviolet radiation of an appropriate wavelength to nick the DNA. In this and other embodiments an appropriate wavelength is a wavelength of ultraviolet radiation which is absorbed by the ligand bands of the complex used.

Still another embodiment of this invention is a method for killing a portion of a population of appropriate tumor cells. The method involves contacting the tumor cells under suitable conditions with an effective amount of a coordination complex of the formula $(R)_2—M—(Y)_2$, as previously defined, to kill the tumor cells. In a presently preferred embodiment, the suitable transistion metal, M, is cobalt(III). If the tumor cells are present in a subject, e.g. a human or animal, the tumor cells may be contacted with the coordination complex by administering the complex to the subject. When a cobalt(III)-containing complex is used, the method may further involve irradiating the tumor cells with a suitable dose of ultraviolet radiation, as previously defined, at a suitable time after the tumor cells have been contacted with the complex, permitting the complex to nick DNA.

This invention further concerns a pharmaceutical composition for the treatment of tumor cells in a subject. The composition comprises an effective anti-tumor amount of a complex of the formula $(R)_2—M—(Y)_2$, as defined above, and a pharmaceutically acceptable carrier. Preferably, the suitable transition metal, M, is ruthenium (II) or cobalt (III), with cobalt (III) being especially preferred. Suitable carriers include sterile saline or buffer-containing solutions or other carriers known in the art such as those used with cisplatin.

Still another embodiment of this invention is a method for treating a subject, e.g. a human or animal, afflicted with tumor cells so as to cause regression of the tumor cells. The method involves administering to the subject by a suitable route a pharmaceutical composition as described above in an amount sufficient to cause regression of the tumor cells. Suitable routes of administration include parenteral administration and topical administration, e.g. in cases such as skin cancers where the tumor cells are located on or near an exposed surface of the subject. Furthermore, if the complex used is a cobalt (III)-containing complex, the method may additionally involve irradiating the tumor cells with a suitable dose of ultraviolet radiation of an appropriate wavelength permitting the complex to nick DNA. In this method the irradiation should be conducted at a suitable time after administration of the composition to the subject, i.e. to permit the complex to interact with the DNA.

EXPERIMENTAL DETAILS

Unlike the corresponding tris-substituted complexes, the bis-analogues of this invention are not coordinatively saturated. The cis-oriented chlorides are good leaving groups, permitting DNA base substitution at those positions. Indeed the aqueous chemistry of ruthenium(II), and bis(1,10-phenanthroline)dichlororuthenium(II) [also referred to as $(phen)_2RuCl_2$] in particular, resembles reactions of platinum(II). The complex $(phen)_2RuCl_2$ binds covalently to DNA. The neutral ruthenium complex moreover shows similarities to the anticancer drug cis-dichlorodiammineplatinum(II) (cis-DDP) in its binding characteristics, with respect to rates of reaction, DNA conformational changes, and the preferential binding to guanine sites. The ruthenium complex offers two potentially interesting advantages. First, the enantiomers show chiral selectivity. The complexes represent covalent-binding analogues to the chiral tris-phenanthroline cations. One enantiomer binds preferentially to right-handed B-DNA. The other enantiomer binds to left-handed DNA preferentially and even converts sequences from the B- to Z-form. Secondly the organic ligand framework for these octahedral complexes permits additional specificity to be built in. Thus the stereochemistry in these ruthenium complexes provides a basis for the design of site-specific covalent binding drugs.

One illustrative embodiment, namely $(phen)_2RuCl_2$, binds covalently to the DNA duplex and exhibits striking enantiomeric selectivity, different from that observed in the intercalation of corresponding $M(phen)_3$ complexes with DNA.

In one experiment, racemic $(phen)_2RuCl_2$ (7) (50 $\mu$M) was incubated in buffer containing 10% ethanol, 50 mM NaNO$_3$, 5 mM Tris at pH 7.1, either at ambient temperatures or 37° C. for variable amounts of time with calf thymus DNA (500 μM nucleotide) (8). Immediately after the incubation period, NaCl and 95% ethanol were added to quench the reaction and precipitate the DNA. Unbound ruthenium, more soluble in the ethanol supernatant, remained in solution. After centrifugation, the supernatant was assayed spectrophotometrically, compared to controls lacking ruthenium or DNA, and levels of bound and free metal complex were determined. This experiment measured only covalent binding to the DNA.

The procedure was repeated using the coordinatively saturated tris(phenanthroline) ruthenium cation, (phen)$_3$Ru$^{2+}$, which binds to DNA by intercalation (4). Under these assay conditions no binding to DNA was observed. A plot of the extent of coordination to DNA by the (phen)$_2$Ru$^{2+}$ cation as a function of time is shown in FIG. 1. A maximum binding ratio of 0.045, or one (phen)$_2$Ru$^{2+}$ moiety for every 11 base pairs, is obtained at about 3½ hours. This dependence on time likely reflects both the kinetics of hydrolysis of (phen)$_2$RuCl$_2$ and ligand substitution (9), e.g. the association of the metal complex with the DNA.

Figure 2:
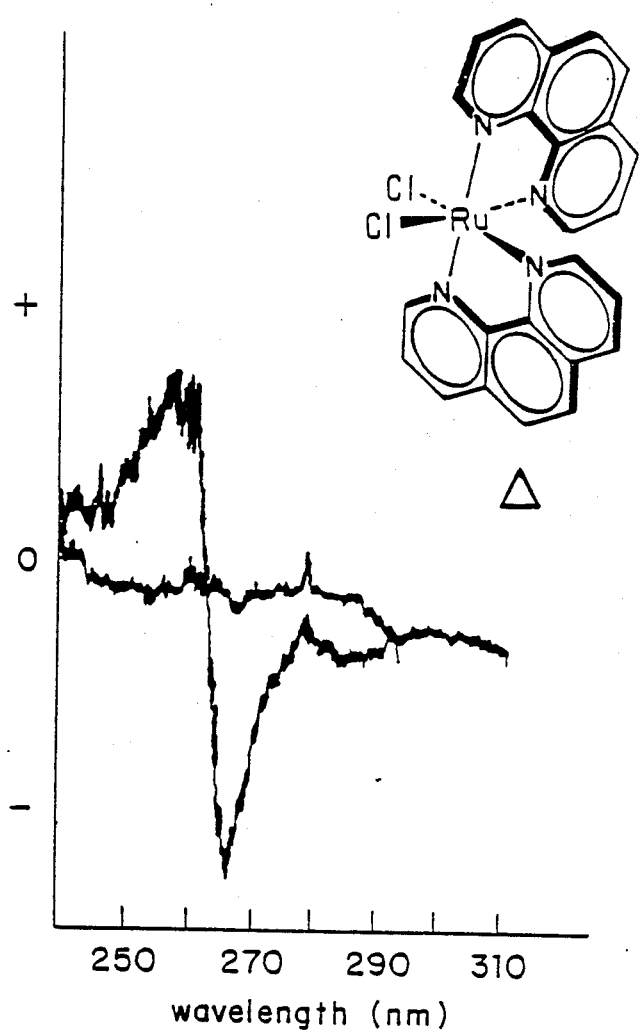
FIG. 2: Circular dichroism of the supernatant after ethanol precipitation of the ruthenium complex bound to B-DNA. Binding to B-DNA is stereoselective and leads to enrichment of the supernatant in the unbound delta isomer (inset).

Significant enantiomeric discrimination accompanies this covalent binding. The circular dichroism of the supernatant, the unbound fraction, is shown in FIG. 2. The solution is appreciably enriched in the less favored isomer. Optically enriched (phen)$_2$RuCl$_2$ solutions have not been obtained previously using more conventional methods. While the rate of racemization of the complexes of this invention is slow in the buffer system used, significant solvent dependence in the racemization rate has been observed. These observations support similar observations previously reported (10). The magnitude of the rotation in the ultraviolet region is approximately 5 times larger than that seen earlier for (phen)$_3$Ru$^{2+}$ solutions at comparable levels of intercalative binding. Hence, the degree of chiral selectivity for this covalent adduct appears substantially greater than for (phen)$_3$Ru$^{2+}$. Based upon exciton theory (11), it was expected that the rotational strength of pure enantiomers of (phen)$_2$RuCl$_2$ in the vicinity of the ligand absorption would be one half that of (phen)$_3$RuCl$_2$. Since pure enantiomers of (phen)$_2$RuCl$_2$ have not been isolated, the relative ratio of affinities of the two enantiomers has not yet been determined. The absolute configuration of the isomer preferred has, however, been assigned. Based upon simple exciton theory (11) and the identical circular dichroism (CD) in the ultraviolet region to that for (phen)$_3$Ru$^{2+}$ (12), the CD given in FIG. 2 has been assigned to the delta isomer. In contrast to the binding specificity seen with (phen)$_3$Ru$^{2+}$, it is lambda-(phen)$_2$Ru$^{2+}$ that binds preferentially to B-DNA.

The enantiomeric discrimination of the bis(phenanthroline) ruthenium complex in binding to B-DNA must therefore differ from tris(phenanthroline) cation not only in degree but also in the structural basis for the stereoselectivity. Ruthenium(II) complexes have a high affinity for the heterocyclic bases of DNA (14). A likely site of metallation would be the N-7 atom of guanine, which is readily accessible in the major groove of the DNA duplex. Initial intercalation is probable; immediate hypochromic changes in the ruthenium charge transfer band are evident upon the addition of DNA. However further spectroscopic changes become evident on a time scale comparable to the binding given in FIG. 1 and these changes must reflect covalent binding to the helix. From an initially intercalated position, the lambda isomer is well oriented for covalent binding to base positions above and below. Model building shows that the delta isomer cannot be similarly aligned for covalent binding, since the other non-stacked phenanthroline ligand is considerably crowded by the right-handed helical column (base and sugar-phosphate groups). This bifunctional coordination oriented by initial intercalation could account for the high stereoselectivity observed. It is interesting that in the case of intercalation by (phen)$_3$Ru$^{2+}$, the delta isomer, which has the same helical screw sense as the right-handed B-DNA, is preferred, while here metallation of base positions seems to require the lambda configuration, that is a structure complementary to the B-DNA helix.

Recently the photoactivated stereospecific cleavage of DNA by chiral tris-substituted phenanthroline complexes of Cobalt(III), e.g. the tris (4,7-diphenyl-1,10-phenanthroline) or "DIP" cobalt complexes, has been reported (6). The corresponding chiral bis enantiomers, e.g. bis(DIP)Co(III) tartrate, which have DNA binding properties analogous to those of the corresponding bis-ruthenium complexes have now been found to cleave DNA photochemically and at sites different from (DIP)$_3$Co$^{+3}$. Bis(DIP)Co(III) for example may cleave DNA specifically at homopurine sites upon ultraviolet irradiation.

The stereoselective covalent binding to DNA of (phen)$_2$RuCl$_2$, substituted analogs thereof, e.g. the bis-DIP complex, and the corresponding cobalt analogues likely has significant biological consequences. The neutral (phen)$_2$RuCl$_2$, for example, may be considered an octahedral analogue for cis-Pt(NH$_3$)$_2$Cl$_2$ (14). Results from laboratories in Australia more than ten years ago which indicated antibacterial, virostatic, and antileukemic activity in vitro of tris unsubstituted phenanthroline complexes of ruthenium(II) (15); recent reports of antitumor activities and toxicities of various ruthenium complexes (1,15), the possible similarities between Ru(phen)$_2$Cl$_2$ and cis-DDP in interactions with DNA; and the striking stereoselectivity observed with the complexes of this invention all support potential chemotherapeutic application of these chiral complexes.

Complexes of this invention have in fact been screened with respect to cytotoxicity, and the results presented in Table I show the complexes to be highly potent in vitro. Additionally, the cobalt complexes of this invention may exhibit photochemical activation with ultraviolet irradiation.

These compounds are potentially very effective antitumor drugs. The advantages such compounds provide over cis-platin include lower heavy-metal toxicity, greater selectivity owing to stereochemistry, greater site specificity given the organic ligands (not present in cis-platin) and the possibility of linkage to monoclonal antibodies, and easier and less expensive preparation. Furthermore the cobalt(III) nicking activity may permit localization by photolysis in vivo.

TABLE I

| Cytoxicity Results of Cobalt and Ruthenium Complexes | | |
|---|---|---|
| Compound | Cell Line[a] | ID$_{50}$ (μg/ml)[b] |
| Ru(phen)$_2$Cl$_2$ | L1210 | 4.7 |
|  | P815 | 7.0 |
| Ru(DIP)$_2$Cl$_2$ | L1210 | 3.2 |
|  | P815 | 3.5 |
| Co(DIP)$_2$Cl$_2$ | L1210 | 0.44 |

TABLE I-continued

Cytoxicity Results of Cobalt and Ruthenium Complexes

| Compound | Cell Line[a] | ID$_{50}$ ($\mu$g/ml)[b] |
|---|---|---|
| | P815 | 0.48 |

[a]L1210 and P815 are mouse leukemia cell lines
[b]determined by the method of Burchenal, J.H. et al., CANCER RESEARCH 42:2598–2600 (1982)

EXPERIMENTAL METHOD AND MATERIALS

Phenanthroline Complexes

Racemic (phen)$_2$Ru(II)Cl$_2$ was prepared as follows: To a solution of 3 mmoles RuCl$_3$.3H$_2$O in 30 ml dimethylformamide was added 6 mmoles phenanthroline monohydrate. The solution was allowed to reflux for 3 h during which time the solution turned a deep violet in color. After being reduced in volume to about 20 ml, the solution was cooled at 0° C. and a deep black solid as crude product was obtained. The product was recrystallized twice from 100 ml 50% ethanol saturated with lithium chloride. Racemic mixtures of other complexes of this invention were prepared by analogous method ssubstituting the appropriate 1,10-phenanthroline compound for 1,10-phenanthroline. See also (7). 1,10-phenanthroline, 4,7-diphenyl-1,10-phenanthroline, and other chemical reagents were obtained from Aldrich Chemical Co., St. Louis, Mo.

Spectroscopic data for Ru(phen)$_2$Cl$_2$ in ETOH was as follows:

$\epsilon = 1.08 \times 10^4 M^{-1} cm^{-1}$ at 496 nm; $\epsilon = 7.25 \times 10^4 M^{-1} cm^{-1}$ at 267 nm. In aqueous solution the complex may be considered a mixture of hydrolyzed species.

Bis (4,7-diphenyl-1,10-phenanthroline)cobalt(III) chloride, (DIP)$_2$Co(III)Cl$_2$, was prepared as follows: 4,7-diphenyl-1,10-phenanthroline (Aldrich) was dissolved in a minimum volume of ethanol to which one half stoichiometric CoCl$_2$.6H$_2$O was added. The green-brown solution was oxidized by using Br$_2$/H$_2$O, and a heavy orange precipitate formed immediately. The solution was refluxed for 1 h, and concentrated hydrochloride was added. The bromine oxidation was then repeated. The crude complex was recrystallized in aqueous ethanol. Other cobalt(III) complexes of this invention may be prepared by this method by substituting the appropriate ligand for 4,7-diphenyl-1,10-phenanthroline.

Buffers and DNA

Calf thymus DNA was obtained from Sigma Chemical Company, St. Louis, Mo. and purified by phenol extraction using previously described methods (8). DNA concentrations per nucleotide were determined spectrophotometrically by assuming $\epsilon_{260} 6000 M^{-1} cm^{-1}$ (18). Buffers were also obtained from Sigma.

DNA cleavage

The cobalt complex is added to the DNA sample in a solution buffered to about 7.1 e.g., in buffer containing 10% ethanol, 50 mM NaNO$_3$, 5 mM Tris at pH 7.1, either at ambient temperature or 37° C. The solution is then irradiated at 315 nm with a 1000 W Hg/xenon lamp (narrowed to 315±5 nm with a monochrometer) for about 90 seconds to about 1 hour and the precipitate washed with ethanol.

In vitro screening

For cell culture studies, a modification of the technique of Fischer (4) was used. The cells were incubated in McCoy's Medium 5A with 15% fetal calf serum. The initial inoculum was 40,000 to 60,000 leukemic cells/ml. For studies of the inhibition of cell growth, 0.1 ml of a 20-fold concentration of the drug in question was added to 2 ml of media containing $4 \times 10^4$ cells/ml in Linbro tissue culture multiwell plates and allowed to incubate at 37° in 5% CO$_2$ for 96 hours. By this time, growth to approximately 10$^6$ cells/ml occurred in the control wells. The contents of each well were agitated to resuspend the cells and counted on a Coulter Counter. The percentage of inhibition of growth and the concentrations inhibiting cell growth by 50% were calculated. Cell culture experiments were done with mouse leukemia cell lines L1210 and P815 which may be obtained from the American Type Culture Collection (ATCC), Rockville, Md.

REFERENCES 1. (a) Lippard, S. J., Ed. "Platinum, Gold, and Other Metal Chemotherapeutic Agents," A.C.S. Sympos. Ser. No. 209; American Chemical Society, Washington 1983; (b) Barton, J. K. and Lippard, S. J., Met. Ions Biol., 1980, 1:31; (c) Marzilli, L. G.; Kistenmacher, T. J.; Eichhorn, G. L., Met. Ions Biol., 1980, 1:179; (d) Martin, R. B. and Mariam, Y. H., Met. Ions. BIol. Syst., 1979, 8:57; (e) Marzilli, L. G., Prog. Inorg. Chem., 1977, 23:255; (f) Hodgson, D. J., Prog. Inorg. Chem., 1977, 23:211.

2. Rosenberg, B.; Van Camp, L.; Trosko, J. E.; Mansour, V. H.; Nature (London), 1969, 222:385; (b) Rosenberg, B.; Van Camp, L., Cancer Res., 1970, 30:1979; (c) for a review, see Hill, J. M.; Loeb, E.; MacLellan, A.; Hill, N. V.; Khan, A.; King, J. J.; Cancer Chemother. Rep., 1975, 59:647; (d) Lippard, S. J., Acct. Chem. Res., 1978, 11:211; (e) Hacker, M. P.; Doyle, E. B.; Krakoff, I. H., Eds. "Platinum Coordination Complexes in Cancer Chemotherapy"; Martinus Nijhoff: Boston 1984.

3. Barton, J. K.; Dannenberg, J. J.; Raphael, A. L., J. Amer. Chem. Soc., 1982, 104:4967.

4. Barton, J. K.; Danishefsky, A. T.; Goldberg, J. M., J. Amer. Chem. Soc., 1984, 106:2172.

5. Barton, J. K.; Basile, L. A.; Danishefsky, A.; Alexandrescu, A.; Proc. Natl. Acad. Sci. USA, 1984, 81:1961.

6. Barton, J. K. and Raphael, A. L., J. Amer. Chem. Soc., 1984, 106:2466.

7. See Sullivan, B. P.; Salmon, D. J.; Meyer, T. J.; Inorg. Chem., 1978, 17:3334.

8. Barton, J. K. and Lippard, S. J., Biochemistry, 1979 12:2661.

9. Isied, S. S. and Taube, H., Inorg, Chem., 1976, 15:3070.

10. Arce Seques, J. A.; Gillard, R. D.; Smalley, D. H.; Williams, P. A.; Inorg. Chim. Acta, 1980, 43:211.

11. Bosnich, B., Acc. Chem. Res., 1968, 2:266.

12. McCaffrey, A. J.; Mason, S. F.; Norman, B. J.; J. Chem. Soc. A, 1969: 1428.

13. (a) Clark, M. J.; Taube, H.; J. Amer. Chem. Soc., 1974, 96:5413; (b) Clarke, M. J., Inorg. Chem., 1977; 16:738; (c) Clarke, M. J.; Buchbunder, M., Inorg. Chim. Acta, 1978, 27:L87; (d) Clarke, M. J., Inorg. Chem., 1980, 19:1103; (d) Graves, B. J.; Hodgson, D. J., J. Amer. Chem. Soc., 1974, 101:5608.

14. The bite size for cis-DDP is 3.35 A and for bis(-diamine)-dichlororuthenium(II) complexes is 3.49 A. See respectively Milburn, G. H. W.; Truter, M. R., J. Chem. Soc. A, 1966: 1609; and Pank, V.; Klaus, J.; von Deuton K.; Feigel, M.; Bruder, H.; tom Dieck, H., Transition Met. Chem., 1981, 6:185.

15. (a) F. P. Dwyer, I. K. Reid, Shulman, G. M. Laycock and S. Dixson *Aust. J. Exp. Biol. Med. Sci.* 47, 203 (1969); (b) F. P. Dwyer, E. Mayhew, E. M. F. Roe, and A. Shulman *Brit. J. Cancer* 19, 195 (1965); (c) A. Shulman and D. O. White *Chem. Biol. Inter.* 6, 407 (1973); (d) A. Shulman and G. M. Laycock *Chem. Biol. Inter.* 16, 89 (1977).

16. (a) Clarke, M. J., Met. Ions Biol. Syst., 1980, 11:231; (b) Giraldi, Sawa, G.; Berloli, G.; Mestroni, G.; Zassinovich, G.; Cancer Res.. 1977, 37:26 (c) Yasbin, R. E.; Matthews, C. R.; Clarke, M. J.; Chem. Biol. Interactions, 1980, 1983, 45:2; Tsuruo, T.; Iida, H.; Tsukagoshi, S. Sakurai, Y.; Jap. J. Can. Res., 1980, 71:151.

17. Wells, R. D. et al., Mol. Biol., 1970, 54:465.

What is claimed is:

1. A method for selectively nicking B-DNA or Z-DNA present within DNA by effecting breakage of at least one phosphodiester bond within the B-DNA or Z-DNA which comprises contacting the B-DNA or Z-DNA with a coordination complex of the formula $(R)_2$—Co(III)—$(Y)_2$, wherein R comprises 1,10-phenanthroline or a substituted derivative thereof, Y comprises a labile ligand and Y and R are bound to the Co(III) by coordination bonds, under conditions such that the complex covalently binds to the B-DNA or Z-DNA stereoselectively to form an adduct and irradiating the adduct so formed with ultraviolet radiation of a wavelength which is absorbed by the ligand bands of the coordination complex so as to selectively nick the B-DNA or Z-DNA.

2. A method for labeling DNA with a complex of the formula $R_2$—M which comprises contacting the DNA with a complex having the formula $(R_2)$—M—$(Y)_2$, wherein R comprises 1,10-phenanthroline or a substituted derivative thereof, M comprises ruthenium (II) or cobalt (III), and Y is a labile ligand and wherein R and Y are bound to M by coordination bonds; the contacting being effected under conditions such that the complex covalently binds to the DNA and thereby labels the DNA with a complex of the formula $R_2$—M.

3. A labeled DNA molecule produced by the method of claim 2.

4. A method of claim 2, wherein the substituted derivative of 1,10-phenanthroline comprises 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline, or 3,8-dispermine-1,10-phenanthroline.

5. A method of claim 2, wherein M is ruthenium (II).

6. A method of claim 2, wherein M is cobalt (III).

7. A labeled DNA molecule comprising a DNA molecule and a complex of the formula $(R)_2$—M, wherein R comprises 1,10-phenanthroline or a substituted derivative thereof, wherein M comprises ruthenium (II) or cobalt (III) and wherein R is bound to M by a coordination bond, the complex being covalently bound to the DNA.

8. A labeled DNA molecule of claim 7, wherein the substituted derivative of 1,10-phenanthroline comprises 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline, or 3,8-dispermine-1,10-phenanthroline.

9. A labeled DNA molecule of claim 7, wherein M is ruthenium(II).

10. A labeled DNA molecule of claim 7, wherein M is cobalt(III).

* * * * *